US011839417B2

(12) United States Patent
Ripplinger

(10) Patent No.: US 11,839,417 B2
(45) Date of Patent: Dec. 12, 2023

(54) DEVICE AND METHOD FOR COAGULATION AND DISSECTION OF BIOLOGICAL TISSUE

(71) Applicant: Erbe Elektromedizin GmbH, Tuebingen (DE)

(72) Inventor: Thomas Ripplinger, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 420 days.

(21) Appl. No.: 17/229,339

(22) Filed: Apr. 13, 2021

(65) Prior Publication Data
US 2021/0315624 A1 Oct. 14, 2021

(30) Foreign Application Priority Data
Apr. 14, 2020 (EP) ..................................... 20169436

(51) Int. Cl.
| A61B 18/00 | (2006.01) |
| A61B 18/12 | (2006.01) |
| A61B 18/14 | (2006.01) |

(52) U.S. Cl.
CPC .......... *A61B 18/00* (2013.01); *A61B 18/1206* (2013.01); *A61B 18/1445* (2013.01);
(Continued)

(58) Field of Classification Search
None
See application file for complete search history.

(56) References Cited

U.S. PATENT DOCUMENTS 4,712,544 A * 12/1987 Ensslin .............. A61B 18/1206
606/39
7,115,121 B2  10/2006 Novak
(Continued)

FOREIGN PATENT DOCUMENTS

| EP | 2992849 A1 | 3/2016 |
| EP | 3132765 A1 | 2/2017 |

(Continued)

OTHER PUBLICATIONS

Extended European Search Report dated Oct. 21, 2020, in corresponding European Application No. 20169436.1, with machine English translation (13 pages).

*Primary Examiner* — Linda C Dvorak
*Assistant Examiner* — Nicholas S Borsch
(74) *Attorney, Agent, or Firm* — Fitch, Even, Tabin & Flannery LLP

(57) ABSTRACT

A device and a method for coagulation and/or dissection of biological tissue is disclosed. The device comprises an apparatus and an instrument electrically connected thereto. The instrument includes an operation circuit with a manually operated switch. An evaluation circuit of the apparatus provides an evaluation signal for the instrument. The apparatus can create a supply voltage or a supply current for the instrument. In the initial condition the evaluation signal comprises only one polarity. The evaluation signal is provided to a control circuit of the instrument in which a characteristic of the evaluation signal is adjusted depending on the operating condition of the switch. The evaluation circuit detects this characteristic and initiates the output of the supply voltage and changes the polarity of the evaluation signal according to the requested cutting mode. In the cutting mode the evaluation signal comprises at least temporarily also a second polarity.

16 Claims, 8 Drawing Sheets

(52) U.S. Cl.
CPC ............ *A61B 2018/0072* (2013.01); *A61B 2018/00607* (2013.01); *A61B 2018/00642* (2013.01); *A61B 2018/00767* (2013.01); *A61B 2018/00928* (2013.01)

(56) References Cited

U.S. PATENT DOCUMENTS

| | | | |
|---|---|---|---|
| 2012/0265196 A1* | 10/2012 | Turner | H01H 1/00 606/34 |
| 2016/0066980 A1 | 3/2016 | Schall et al. | |
| 2017/0049505 A1* | 2/2017 | Weiler | A61B 18/1445 |

FOREIGN PATENT DOCUMENTS

| | | |
|---|---|---|
| WO | 02/100283 A1 | 12/2002 |
| WO | 2019/126370 A1 | 6/2019 |

\* cited by examiner

DEVICE AND METHOD FOR COAGULATION AND DISSECTION OF BIOLOGICAL TISSUE

RELATED APPLICATION(S)

This application claims the benefit of European Patent Application No. 20169436.1, filed Apr. 14, 2020, the contents of which are incorporated herein by reference as if fully rewritten herein.

TECHNICAL FIELD

The invention refers to a device and a method for coagulation and dissection of biological tissue. The device comprises an instrument and an apparatus supplying the instrument with electrical energy.

BACKGROUND

Such a device is known from EP 3 132 765 A1 for example. The instrument has a tool with a cutting electrode and multiple coagulation electrodes. The electrodes can be supplied with electrical energy by means of an operation circuit. For this the operation circuit comprises a transformer that is connected on its secondary side with the cutting electrode via a power switch. The instrument has a cutting activating switch and a coagulation activating switch. The coagulation activating switch is mechanically coupled with a power switch. During operation of the coagulation activating switch the electrical connection between the cutting electrode and the transformer is interrupted or switched such that no cutting voltage is applied to the cutting electrode.

WO 2019/126370 A1 describes a device and method for coagulation and cutting of biological tissue. The device has an apparatus having a sealing stage and a cutting stage for electrical supply of a connected instrument having a coagulation with a coagulation voltage for sealing or a cutting voltage for cutting. Both stages respectively comprise a converter for a voltage control and can be operated independent from one another. For cutting the sealing voltage is provided first in a first-time interval and subsequently in a second-time interval the cutting voltage is provided.

The instruments used for coagulation and cutting can be single-use or reusable instruments. Particularly with single-use instruments the manufacturing costs play a major role. A safe handling must be guaranteed.

Therefore, it can be considered an object of the present invention to provide an instrument that can be handled in a simple and safe manner and that can be cheaply manufactured.

SUMMARY

This object is solved by a device and a method as disclosed herein.

The inventive device comprises an apparatus and an instrument that is electrically connected with the apparatus. By means of the instrument, biological tissue can be sealed (coagulation) and/or cut (dissection). For this the instrument comprises respective electrodes.

The apparatus is configured to provide a supply voltage or a supply current for the instrument at an apparatus output. In addition, the apparatus comprises an evaluation circuit that is configured to provide an evaluation signal for the instrument at a second apparatus output.

The instrument has an operation circuit having a supply connector for connection with the first apparatus output and having a signal connector for connection with the second apparatus output. A control circuit is electrically connected with the signal connector and is configured to create a control signal that depends on the polarity of the evaluation signal provided by the apparatus. In addition, the control circuit has a first switch that can be manually operated. According to the example the first switch serves for activating the cutting mode of the device.

In addition, the operation circuit of the instrument comprises a switch unit that can be controlled by means of the control signal. The switch unit can take a first switch condition or a second switch condition. The switch unit is directly or indirectly connected with the supply connector and directly or indirectly connected with the cutting output. Depending on the polarity of the evaluation signal, a control signal is generated that causes the switch unit to take either the first or the second switch condition.

In a preferred embodiment the switch unit can be arranged in series between the supply connector and the cutting output. In this configuration the switch unit can be switched between a conducting first switch condition and a blocking second switch condition, for example. Alternatively, the switch unit can also comprise a conducting first and a conducting second switch condition, wherein either a coagulation voltage or a cutting voltage is applied to the cutting output depending on the switch condition, depending on whether the instrument or the device shall be operated in the coagulation mode or the cutting mode.

In the first switch condition of a switch unit an electrical cutting voltage or an electrical cutting current is provided at the cutting output that is appropriate for cutting of biological tissue. On the contrary, in the second switch condition no electrical cutting voltage or no electrical cutting current is available at the cutting output that is sufficient for cutting of biological tissue. In the second switch condition either a voltage or a current of substantially equal to zero can be provided at the cutting output or alternatively a voltage or a current can be provided at the cutting output that is insufficient for cutting, but for example appropriate for coagulation.

The control circuit is configured to adjust or modify a characteristic of the evaluation signal depending on the operation condition of the first switch. For example, the characteristic of the evaluation signal can be an amount, an amplitude, an average value or the like. The characteristic is preferably independent from the polarity of the evaluation signal. In a preferred embodiment the amount of an evaluation current flowing through the control circuit can be used as characteristic, for example, that characterizes whether the first switch is operated or non-operated.

The apparatus of the device is in turn configured to detect the characteristic of the evaluation signal, e.g. the amount of the evaluation current, influenced or adjusted by the control circuit. Thereby the apparatus can determine whether the first switch for activation of the cutting mode is operated or non-operated. Depending on the detected characteristic of the evaluation signal, the polarity of the evaluation signal is in turn adjusted by the evaluation circuit.

Due to the polarity of the evaluation signal, the condition of the control signal is in turn defined and if necessary, changed. Thus, the control signal can be created based on the polarity of the evaluation signal and in so doing the switch unit can be caused to take the first or the second switch condition, such that the device is operated in the desired coagulation mode or cutting mode.

The signal processing by means of the control circuit and the evaluation circuit is very simple and can be cheaply realized. Complex mechanical devices for coupling the switch unit and the control circuit can be omitted. The control is carried out electrically and/or optically by the control signal. The device can be built in a simple manner with standard components.

In an embodiment the switch unit can comprise or can be formed by one or more semiconductor switches. At least mechanical switches can be omitted in the switch unit. In turn this avoids spark or arc creation when changing the switch condition.

The instrument of the device can be a single-use instrument or a reusable instrument. In both cases the instrument can be simply configured and thus manufactured cheaply.

If the evaluation signal adjusted by the control circuit indicates that the first switch is operated, the evaluation signal can comprise different polarity conditions during different phases. Preferably in the cutting mode with operated first switch the evaluation signal has exclusively a first polarity during a first phase starting with the operation of the first switch. Particularly, the amount of the evaluation signal can be constant during the first phase.

A second phase can follow directly after the first phase in which the evaluation signal alternatively or alternatingly comprises the first polarity and a second polarity that is opposed to the first polarity. The first polarity can be negative, for example, and the second polarity can be positive, for example, or vice versa.

For example, the evaluation signal can be a current or a voltage. During a first phase a direct current or a direct voltage can be provided as evaluation signal, for example, and during a second phase an alternating voltage or an alternating current can be provided as evaluation signal, for example. The signal shape during the second phase can vary and can be, for example, a square wave signal, a triangular signal or a sinusoidal signal. During the second phase the evaluation signal can have positive and negative half-waves that can comprise equal durations or different durations and/or equal amplitudes or different amplitudes.

During the second phase the signal portions of the evaluation signal having the first polarity can be used to evaluate the operating condition of the first switch and the signal portions having the second polarity can be used to maintain the switch unit in the desired switch condition by means of the control signal.

Particularly, the control circuit is configured to switch the switch unit by means of the control signal in the first switch condition, if the evaluation signal comprises at least temporarily the second polarity during the second phase. In this first switch condition an electrical cutting voltage is applied at the cutting output or an electrical cutting current is provided.

If the evaluation signal comprises only the first polarity during the first phase, the switch unit is caused to take the second switch condition by means of the control signal. The control signal can be substantially zero, if the evaluation signal comprises the first polarity. In the second switch condition no voltage or current is available at the cutting output that could carry out cutting of biological tissue.

In a preferred embodiment the apparatus can comprise a controllable energy source (current source or voltage source) in order to provide the supply voltage or supply current at the first apparatus output. The evaluation circuit of the apparatus can be configured to control the energy source by means of an activation signal. For example, the supply voltage or the supply current can be switched on or switched off by means of the activation signal.

It is advantageous, if the control circuit comprises a manually operable second switch in addition to the first switch. The second switch can serve for activation of a coagulation mode. In an embodiment of the invention the two switches can be configured such that they can be operated independent from each other, i.e. individually respectively or also concurrently. As an alternative to this, both switches can also be coupled mechanically such that only one of the two switches can be operated at a time as, for example, in the case of a rocker switch.

In a preferred embodiment the first switch and the second switch are configured as button respectively. For example, the buttons can take a blocking condition in their initial condition and can be manually switched in conducting condition.

It is advantageous, if the control circuit is configured to adjust the characteristic of the evaluation signal depending on the operation condition of the second switch. For example, the amount of the evaluation signal can vary depending on whether none of the switches or only the first switch or only the second switch or both switches are operated. Depending on which switch operation has been detected in the evaluation circuit of the apparatus based on the characteristic of the evaluation signal, the polarity thereof is adjusted. In an embodiment the cutting mode having a phase of alternating polarity of the evaluation signal is only activated, if exclusively the first switch has been operated. In all other cases the evaluation signal can exclusively have the first polarity.

It is also advantageous, that the evaluation circuit is configured to create the activation signal for switching on or providing the supply voltage or the supply current at the first apparatus output, if it has been detected based on the characteristic of the evaluation signal that one of the two switches has been operated.

In one embodiment the instrument can have at least one cutting electrode, at least one first coagulation electrode and at least one second coagulation electrode. For example, the cutting output can be connected with the at least one cutting electrode. A first coagulation output of the operation circuit can be connected with the at least one first coagulation electrode. A second coagulation output of the operation circuit can be connected with the at least one second coagulation electrode.

In a preferred embodiment the control circuit comprises a control element that is configured for creation of the control signal.

It is advantageous, if the operation circuit comprises a coupling device that comprises a transmitter component and a receiver component being galvanically separated from the transmitter component. By means of the transmitter component the control signal can be transmitted from the control circuit to the receiver component that is connected with the switch unit or is part of the switch unit.

In an embodiment the transmitter component is a control element. In doing so, the receiver component can be connected with a control port of a controllable semiconductor switch of the switch unit.

For example, at least one light emitting diode can be used as transmitter component and at least one photodiode can be used as receiver component. For example, the transmitter component and the receiver component can be arranged as common unit in a common housing. This unit can be an optocoupler, for example.

It is advantageous, if the receiver component is connected with the control port of the switch unit via a load and unload circuit. In case of a cutting request (e.g. operating of first switch) it is possible to also maintain the first switch condition of the switch unit by means of the load and unload circuit during the time duration during which a first half-wave is applied. Preferably the load and unload circuit is also configured to dissipate the electrical charge in the at least one control port of the switch unit, if no voltage shall be applied to the cutting electrode that is suitable for cutting, in order to allow switching of the switch unit in the second switch condition.

In an embodiment the switch unit can be configured without mechanical switches and can comprise exclusively semiconductor switches, such as bipolar transistors and/or field effect transistors and/or IGBTs.

It is advantageous, if the first switch and the control element are connected in series in the first circuit branch. The first circuit branch can be connected with the signal connector. In doing so, a current flow through the control element can be inhibited when a first switch is open.

For example, in the first circuit branch a one-way current path can be provided in which the control element is arranged. In this one-way current path the current flow is allowed only in one direction, particularly in the current flow direction, if the second half-wave of the evaluation signal is applied. For this at least one component having a diode function is present in the one-way current path. The component having the diode function can be, for example, the control element itself. Alternatively or additionally, a further component having the diode function, in the simplest case a diode, can be provided in the one-way current path. As an alternative to the diode, also controlled semiconductor switches can be used that only take their conducting condition during a second half-wave of the evaluation signal.

In an embodiment the control element is configured as light-emitting diode. In addition to the light-emitting diode a separate diode can be connected in series to the control element, preferably upstream in current flow direction.

It is advantageous, if a further parallel current path is provided parallel to the one-way current path in the first circuit branch, wherein a resistor can be arranged in the parallel current path, for example. If in the present application a resistor is mentioned, an ohmic resistor is meant as long as indicated to the contrary. The first switch is preferably connected in series to the one-way current path and the parallel current path.

In addition, it is advantageous, if the second switch is arranged in a second circuit branch of the control circuit. The second circuit branch is connected with the signal connector. Preferably a resistor is connected in series to the second switch.

In an embodiment the second switch and the control element are coupled via a connection current path. For example, the connection current path can establish a permanent electrical connection between the second switch and the control element that cannot be disconnected. The connection current path can be configured without components. Particularly the second switch and the connection current path are connected parallel to the control element and the first switch. If the second switch is closed or conductive, a low resistance bypass of the control element is effectuated. Thus, no current flow through the control element can occur, if the second switch is conductive. A low resistance bypass of the control element means a bypass that has such a low resistance value that a voltage at the bypass is substantially equal to zero and is particularly smaller than an activation voltage of the control element, e.g. the forward voltage of a light-emitting diode.

It is in addition advantageous, if the first coagulation output of the operation circuit is connected with the supply connector without switches. For example, a capacitor may be arranged in this connection.

Preferably the operation circuit comprises a transformer circuit having a transformer. The transformer circuit is connected with the supply connector on its primary side and with the cutting output on its secondary side, wherein these connections can be direct or indirect connections. The transformer of the transformer circuit can be configured without galvanic separation as autotransformer. The transformer can alternatively also have a primary side galvanically separated from the secondary side. The transformer circuit is particularly configured to increase the supply voltage applied at the supply connector, e.g. from about 100 Volt to about 450 Volt alternating voltage.

In the embodiments explained above the operation circuit is part of the instrument and can be provided in a housing of the instrument. The operation circuit or parts thereof can in addition or as an alternative to the arrangement in the housing of the instrument also be arranged in a separate module that can be electrically connected with the instrument and can be electrically connected between the apparatus and the instrument, for example. For example, the module can be a plug module that can be releasably electrically and/or mechanically connected with the apparatus and the instrument. It can also be arranged in the connection line or cable of the instrument.

Another independent aspect of the invention is characterized by an electrosurgical instrument that is configured to seal biological tissue in a coagulation mode and to cut biological tissue in a cutting mode. The instrument has a switch unit that is electronically and/or optically controlled that comprises at least one semiconductor switch. The switch unit can provide an electrical parameter (cutting voltage and/or cutting current) suitable for cutting of biological tissue at a cutting electrode in a first switch condition. On the contrary, no electrical cutting voltage or no electrical cutting current is available at the cutting electrode in a second switch condition of the switch unit that is sufficient for cutting of biological tissue. In the cutting mode the control of the switch unit is such that the switch unit takes the second switch condition at least during a phase and preferably prior to cutting. In the coagulation mode the switch unit remains continuously in the second switch condition. An electrical and/or optical control signal for control of the switch unit can be created by the instrument, e.g. based on the above-explained evaluation signal and/or another signal and/or a condition of an apparatus for electrical supply of the instrument with which the instrument is connected and that can be detected by the instrument or as an alternative also independent from the apparatus.

This further aspect can be combined with one or more features of the device explained above and particularly the configuration of the above described instrument according to the aspect of the invention that was explained first.

A method for operating a device for coagulation and cutting of biological tissue, particularly by using one of the above-explained embodiments, comprises the following steps:

First, an evaluation signal is created and provided at the second apparatus output for the instrument and particularly the control circuit at the second apparatus output. Preferably, the evaluation signal comprises only the first polarity in an initial condition.

The evaluation signal is received at the signal connector. Depending on the operating condition of the first switch and the optionally provided second switch, a characteristic of the evaluation signal is changed that can be detected by the evaluation circuit. The characteristic of the evaluation signal detected by the evaluation circuit can be, for example, the amount of an evaluation current flowing through the control circuit due to the evaluation signal. This characteristic indicates whether the first switch or the optionally provided second switch has been operated and thus whether the device shall be operated in the cutting mode (e.g. first switch is operated) or in the coagulation mode (e.g. second switch is operated). The polarity of the evaluation signal is adjusted depending on the detected characteristic of the evaluation signal and thus depending on the operation condition of the at least one switch.

Based on the adjusted polarity of the evaluation signal, the control signal for the switch unit is created in turn such that it is either caused to take the first switch condition or to take the second switch condition.

BRIEF DESCRIPTION OF THE DRAWINGS

Advantageous configurations of the invention are derived from the dependent claims, the description and the drawings. Subsequently, preferred embodiments of the invention are explained in detail with reference to the attached drawings. The drawings show:

DETAILED DESCRIPTION

Figure 1:
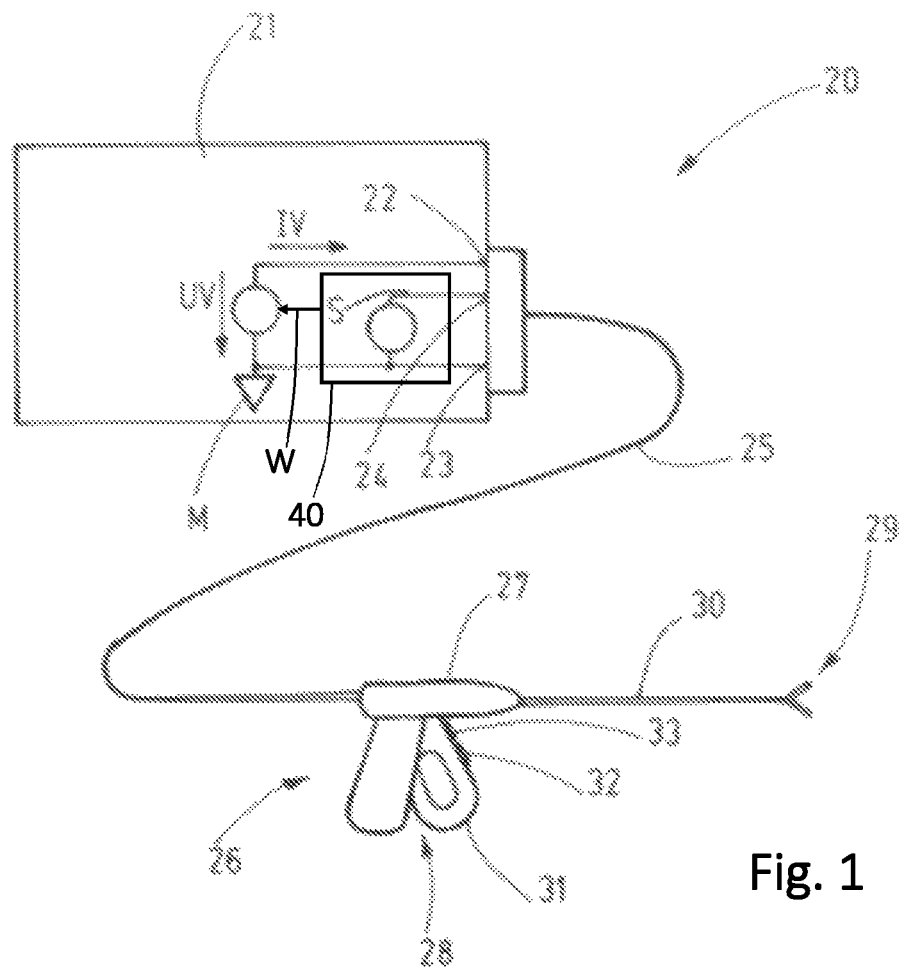
FIG. 1 a schematic illustration of a device for coagulation and cutting having an apparatus and an instrument that is electrically connected with the apparatus, FIG. 2 a perspective partial illustration of a tool of the instrument of FIG. 1, FIG. 3 a circuit diagram of an embodiment of the operation circuit of the instrument, FIG. 4 a schematic illustration of a time progress of an exemplary evaluation signal, FIG. 5 a schematic illustration of a time progress of a coagulation voltage in a cutting mode of the device, FIG. 6 a schematic illustration of a time progress of a cutting voltage in a cutting mode of the device, FIGS. 7-12 a circuit diagram of an embodiment of a control circuit of the operation circuit of FIG. 3 in different conditions, FIG. 13 a circuit diagram of an optional voltage increase circuit for the supply voltage of FIG. 3, FIG. 14 a circuit diagram for a modified embodiment for the switch unit for the operation circuit of FIG. 3, and FIG. 15 a modified embodiment of a circuit part of the control circuit for realizing a diode function by means of a transistor.

FIG. 1 illustrates a device 20 for coagulation and cutting. The device 20 has an apparatus 21 that provides a supply voltage UV or a supply current IV at a first apparatus output 22. For this the apparatus comprises an RF current source or an RF voltage source 42 that is preferably controllable by means of an activation signal W or can be at least switched on and off. An evaluation signal S is provided at a second apparatus output 24. The evaluation signal S is created by an evaluation circuit 40 of the apparatus 21. A third apparatus output 23 is connected with ground M.

Figure 4:
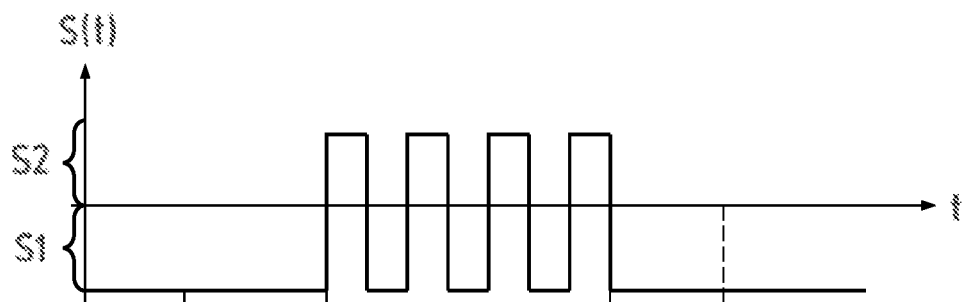

The evaluation signal S is a voltage or a current, for example. It can have a first polarity S1 or a second polarity S2 opposed to the first polarity S1. For example, the first polarity is negative and the second polarity is positive. The polarity S1, S2 of the evaluation signal S can be constant during phases and can be alternating during phases (FIG. 4). The evaluation signal S is illustrated as square wave signal in FIG. 4. Alternatively to this the evaluation signal S could have any other wave shapes during a phase with alternating polarity S1, S2 as well, e.g. a sinusoidal or triangular wave shape with positive and negative half-waves. During a phase with alternating polarity S1, S2, the evaluation signal S can be periodic or aperiodic. It is also possible that the duration for a half-wave with first polarity and a duration for a half-wave with second polarity have different lengths.

Preferably the evaluation signal S has exclusively one polarity, e.g. the first polarity S1 in an initial condition. Thereby the evaluation signal can have a constant amount.

An instrument 26 for coagulation and cutting is connected with the apparatus 21 via a multi-core cable 25. The instrument 26 has a housing 27 having a handle 28 as well as a tool 29. In the embodiment the tool 29 is connected with the housing 27 by a connection part 30. The connection part 30 can be configured in a rod-like manner. An operating element 31 for the tool 29 is present on the handle 28. The operating element 31 serves for mechanical and electrical operation of the tool 29. A manually operable first switch 32 and a manually operable second switch 33 are provided on the operating element 31. In the embodiment the two switches 32, 33 are configured as push-buttons and take an electrically non-conducting condition in their non-operated initial condition.

Figure 2:
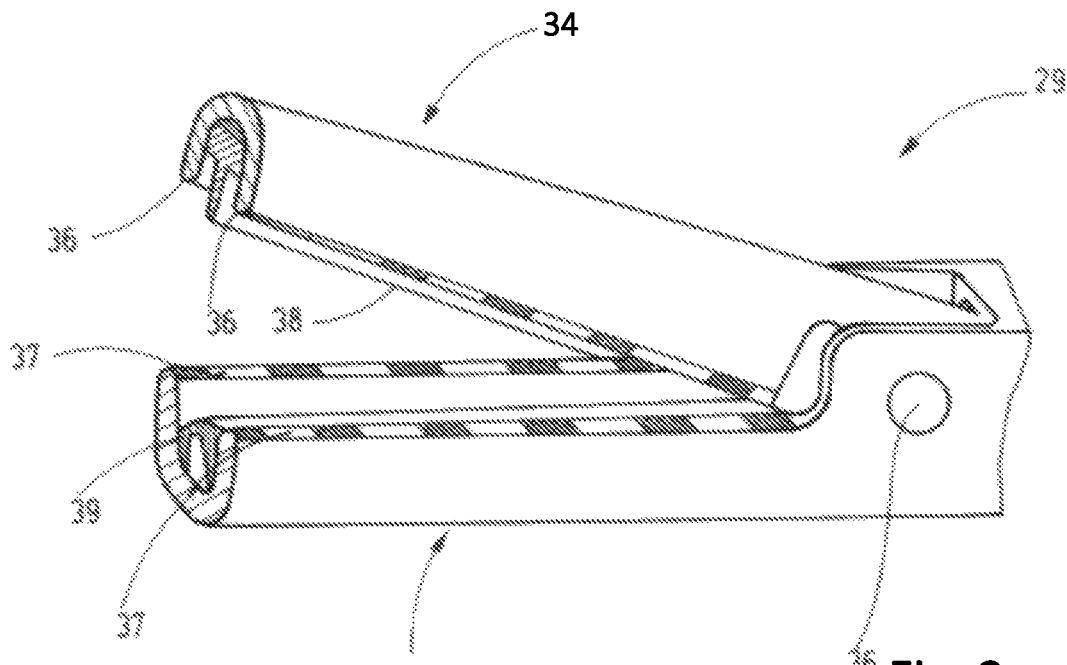

In FIG. 2 the tool 29 of the instrument 26 of FIG. 1 is illustrated in a perspective partial illustration. The tool 29 has two jaws 34, 35 that can be moved relative to one another and that are connected with each other in a hinged manner by means of a hinge 41. The jaws 34, 35 can be pivoted relative to each other by means of the operating element 31. At one of the jaws 34 at least one first coagulation electrode 36 is arranged, whereas at least one second coagulation electrode 37 is provided at the respective other jaw 35. One first coagulation electrode 36 and one assigned second coagulation electrode 37 respectively form a coagulation electrode pair. Multiple coagulation electrode pairs can be provided on the jaws 34, 35.

Furthermore, one of the jaws 34 comprises a cutting electrode 38 in addition. In the embodiment the cutting electrode 38 is arranged as insert in a groove-like depression at the jaw 35 and flanked by two first coagulation electrodes 36. The cutting electrode 38 is arranged on the tool 39 electrically isolated from the first coagulation electrodes 36. The multiple first coagulation electrode 36 can be electrically connected with each other.

A counter support 39 for the cutting electrode 38 is arranged on the jaw 38. If the tool 29 is closed by the operating element 31, one first coagulation electrode 36 and one second coagulation electrode 37 are arranged opposite one another respectively. A cutting electrode 38 is located next to or is in contact with the counter support 39. The electrical functions of the electrodes 36, 37, 38 can be operated by means of the switches 32, 33.

Figure 3:
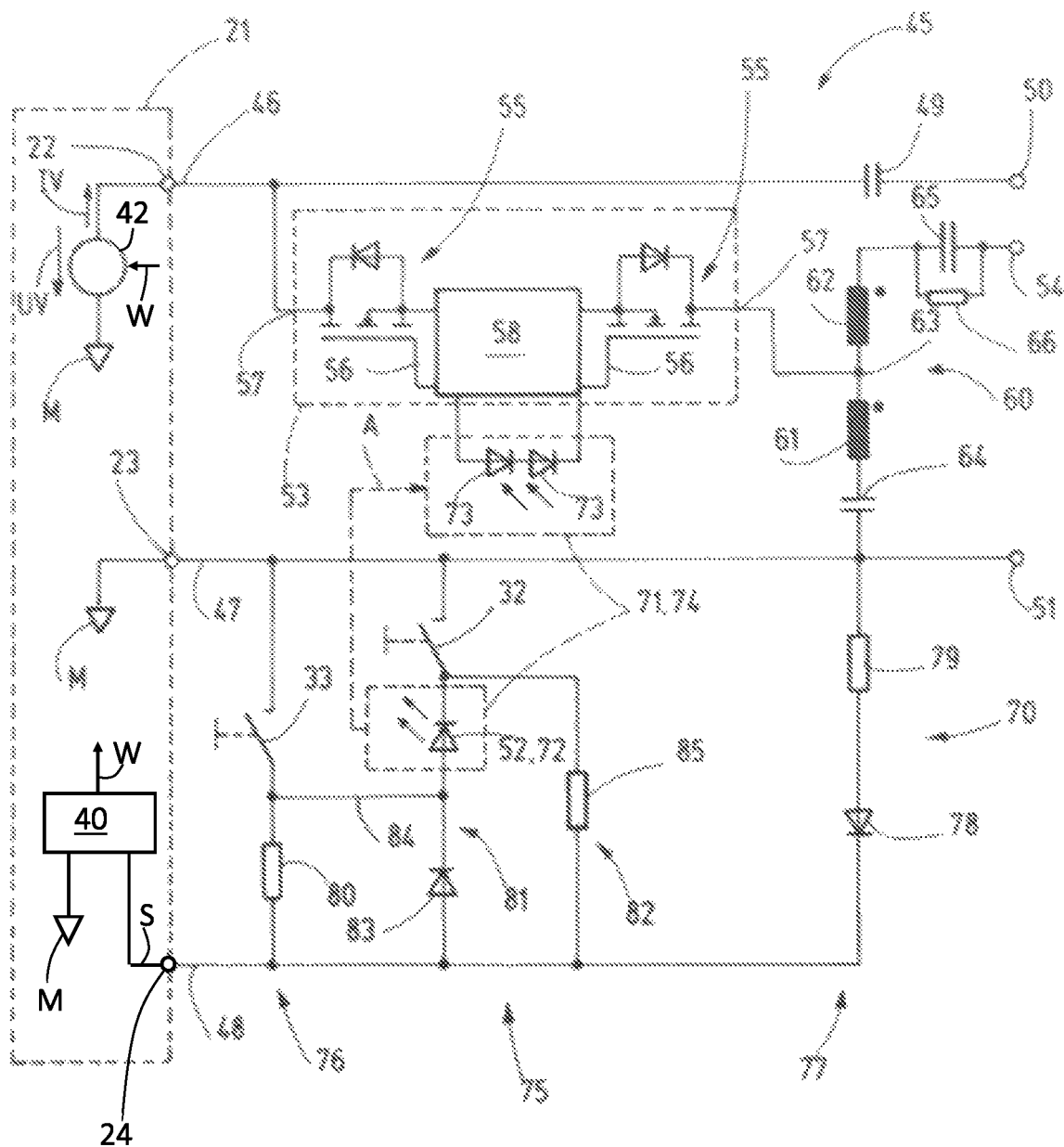

An embodiment of an operation circuit 45 of the instrument 26 is illustrated in FIG. 3. The operation circuit 45 has a supply connector 46 by means of which the operation circuit 45 can be connected with the first apparatus output 22 as well as a ground connector 47 by means of which the operation circuit 45 can be connected with the third apparatus output 23. A signal connector 48 of the operation circuit 45 can be connected with the second apparatus output 24. Thus, the evaluation signal S of the apparatus 21 is provided at the signal connector 48. The operation circuit 45 is connected with ground M via the ground connector 47. The supply connector 46 is connected to the RF current source or RF voltage source 42 of the apparatus 21 according to the example in order to provide a supply current IV or a supply voltage UV for the operation circuit 45.

The supply connector 46 is connected with a coagulation output 50 via a first capacitor 49. The first coagulation output 50 is connected with the at least one first coagulation electrode 36. A second coagulation output 51 is connected with the at least one second coagulation electrode 37. In the embodiment the second coagulation output 51 is configured as ground output. For this the second coagulation output 51 is connected with the ground connector 47 and thus with ground M.

In addition, the operation circuit 45 comprises a switch unit 53 that can be switched by means of a control signal A of a control element 52. The switch unit 53 is connected in the electrical connection between the supply connector 46 and a cutting output 54. The switch unit 53 is configured to provide a cutting voltage US and/or a cutting current at the cutting output 54 in a first switch condition that is configured for cutting by using the cutting electrode 38 and to substantially provide no electrical energy at the cutting output 54 in a second switch condition. According to the example, the connection between the supply connector 46 and the cutting output 54 is interrupted in the second switch condition.

The switch unit 53 is configured without mechanical switches and comprises at least one semiconductor switch 55 and in the embodiment two semiconductor switches 55 that are connected in series. According to the example, each of the semiconductor switches 55 is a field effect transistor that is illustrated here as normally non-conducting n-channel MOSFET. Each semiconductor switch 55 has a control port 56 that is formed by the gate of the MOSFETs according to the embodiment.

Figure 13:
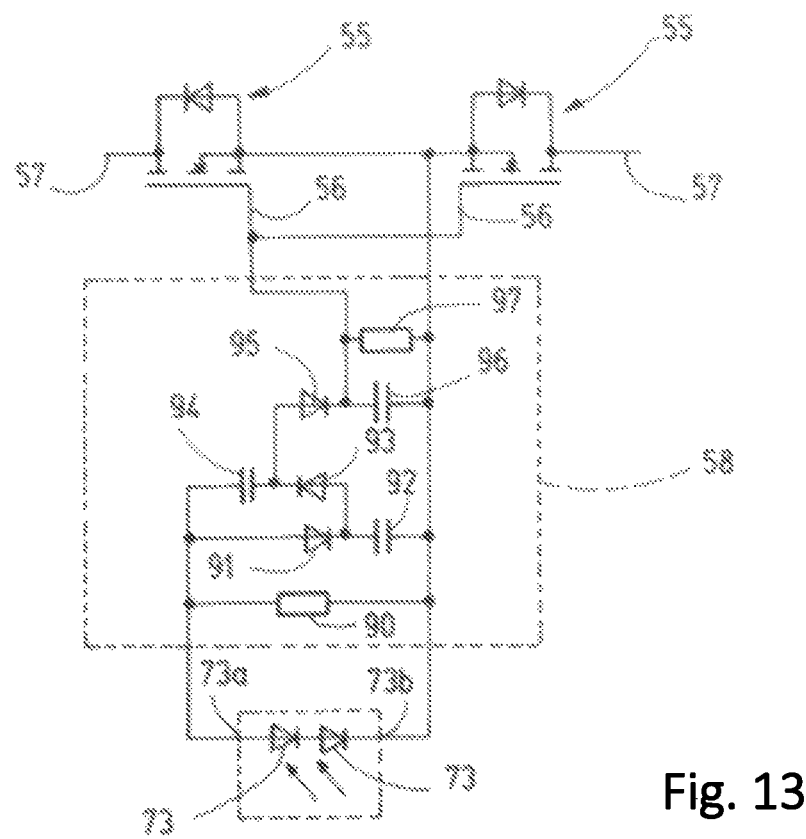

The two control ports 56 are preferably connected with each other. In addition, the two source connections of the MOSFETS can be connected with each other (FIG. 13). The drain connections of the two MOSFETs form a switch port 57 of the switch unit 53 in each case. The switching path of the switch unit 53 is formed between the two switch ports 57. One of the switch ports 57 of the switch unit 53 is connected with the supply connector 46. The respective other switch port 57 is connecting with the cutting output 54.

According to the example, the switch unit 53 comprises a load and unload circuit 58 for the at least one semiconductor switch 55. The load and unload circuit 58 is configured to be able to maintain an electrical charge at the control ports 56 sufficiently long in order to maintain the first switch condition of the switch unit 53 during a phase with alternating polarity S1, S2 of the evaluation signal S as long as the first switch 32 is operated. According to the example, the control signal A for maintaining the first switch condition is created only, if the evaluation signal S has one of the two polarities S1 or S2 and according to the example, the second polarity S2. This results in that during a phase with alternating polarity S1, S2 of the evaluation signal S also the control signal A changes its condition alternatingly. During such a phase the load and unload circuit 58 avoids alternated switching of the switch unit 53 between the first and second switch condition.

In addition, the load and unload circuit 58 is configured to dissipate the charges present at the control ports 56, if the first switch 32 is no longer operated such that the semiconductor switches 55 can again transition into their non-conductive conditions (that corresponds to the second switch condition according to the example).

In the embodiment the operation circuit 45 has a transformer circuit having a transformer 60. The transformer 60 comprises a primary winding 61 and a secondary winding 62. In the embodiment the transformer 60 is configured as autotransformer. Thereby the primary winding 61 and the secondary winding 62 are connected in series and a tap 63 is connected with an assigned switch port 57 of the switch unit 53. Starting from the tap 63 a series connection of the primary winding 61 and a second capacitor 64 is connected with ground M. Starting from tap 63 a series connection of the secondary winding 62 and a third capacitor 65 is connected with a cutting output 54. A first resistor 66 is connected parallel to the third capacitor 65. The parallel connection of the third capacitor 65 and the first resistor 66 forms a spark detection circuit. If sparks occur, the supply current IV comprises a direct current component or the supply voltage UV comprises a direct voltage component that can be evaluated and detected in the apparatus 21 as an option. If such a spark detection is not necessary, the spark detection circuit can also be omitted.

The operation circuit 45 additionally comprises a control circuit 70, wherein the control element 52 is part thereof. The control circuit 70 is coupled with the switch unit 53 via a coupling device 71 in order to transmit the control signal A from the control circuit 70 to the switch unit 53. For this the coupling device 71 has at least one transmitter component 72 in the control circuit 70 and at least one receiver component 73 that is connected with the at least one control port 56 of the switch unit 53. In the embodiment the at least one transmitter component 72 is a light-emitting diode and the at least one receiver component 73 is a photodiode or alternatively a phototransistor. A coupling device 71 can be formed by an optocoupler 74. In the illustrated embodiment the transmitter component 72 is embodied by the control element 52.

In the embodiment shown in FIG. 3 the control circuit 70 comprises a first circuit branch 75 having the first switch 32, a second circuit branch 76 having the second switch 33, as well as a third circuit branch 77. The three circuit branches 75, 76, 77 are connected parallel to each other between the ground connector 47 and the signal connector 48.

In the embodiment the third circuit branch 77 is defined as series connection of a first diode 78 and a second resistor 79. The cathode of the first diode 78 is connected with the signal connector 48 and the anode is connected with the second resistor 79. The other connection of the second resistor 79 is connected with ground M.

The second circuit branch 76 comprises a third resistor 80 in addition to the second switch 33 that is connected in series to the second switch 33.

The first circuit branch 75 has a one-way current path 81 in series to the first switch 32 as well as a parallel current path 82 connected parallel to the one-way current path. In the one-way current path 81 the control element 52 is connected in series to the first switch 32. The one-way current path 81 comprises at least one component having a diode function such that the current can only flow in one direction through the one-way current path 81 and according to the example, from the signal connector 48 toward the ground connector 47, if the first switch 32 is closed. In the embodiment illustrated here an additional component with diode function is connected in series to the control element 52, e.g. a second diode 83. The anode of the second diode 83 is connected with the signal connector 48 and the cathode of the second diode 83 is connected with the control element 52 and according to the example, with the anode of the light-emitting diode forming the control element 52.

In addition, in the illustrated embodiment the connection point between the second diode 83 and the control element 52 is connected with the second switch 33 via a connection current path 84 such that the connection current path 84 and the second switch 33 are connected parallel to the control element 52 and the first switch 32.

In the parallel current path 82 a fourth resistor 85 is connected parallel to the second diode 83 and the control element 52.

The function of the operation circuit 45 is explained subsequently based on FIGS. 4-12. For distinguishing purposes a current flowing through the first circuit branch 75 is referenced as first current I1, a current flowing through the second circuit branch 76 is referenced as second current I2 and a current flowing through the third circuit branch 77 is referenced as third current I3 (FIGS. 7-12). The resistance values of the resistors 79, 85 and 80 in the circuit branches 75, 76, 77 are selected such that the evaluation circuit 40 of the apparatus 21 detects based on the amount of the currents I1, I2, I3 whether the first switch 32, the second switch 33 or both switches 32, 33 is or are in the conductive condition. Particularly the resistance values of the third resistor 80 and the fourth resistor 85 have different amounts.

The control circuit 70 is configured to influence the characteristic of the evaluation signal S provided by the evaluation circuit 40. In the embodiment the amount of an evaluation current that flows between the second apparatus output 24 and the third apparatus output 23 is changed by the control circuit 70 for this purpose depending on the switch condition of the two switches 32, 33. The evaluation circuit 40 can measure the amount of the evaluation current flowing between the second apparatus output 24 and the third apparatus output 23 (ground M), e.g. by means of a measurement resistor.

This possibility to vary the amount of the evaluation current through the control circuit 70 allows simple detection of the switch condition of the first switch 32 and the second switch 33. As an alternative to this, also other characteristics of the evaluation signal S could be modified depending on through which of the circuit branches 75, 76 a current flows, e.g. by changing of the voltage level by means of different dimensioned Zener diodes in the circuit branches 75, 76 or by active components in the circuit branches that modulate the voltage or the current in different manners, etc.

In all cases the evaluation circuit 40 of the apparatus 21 is able to detect whether the first switch 32 and/or the second switch 33 is operated and thus switched in the conductive condition based on the characteristic of the evaluation signal S adjusted by the control circuit 70, such that it can be detected whether an operating person requests a cutting mode or a coagulation mode. By operating the first switch 32, the cutting mode is requested and by operating the second switch 33, the coagulation mode is requested.

In the embodiment the evaluation signal S is constant in an initial condition and exclusively comprises the first polarity S1 that is negative according to the example, as schematically shown in FIG. 4.

Figure 7:
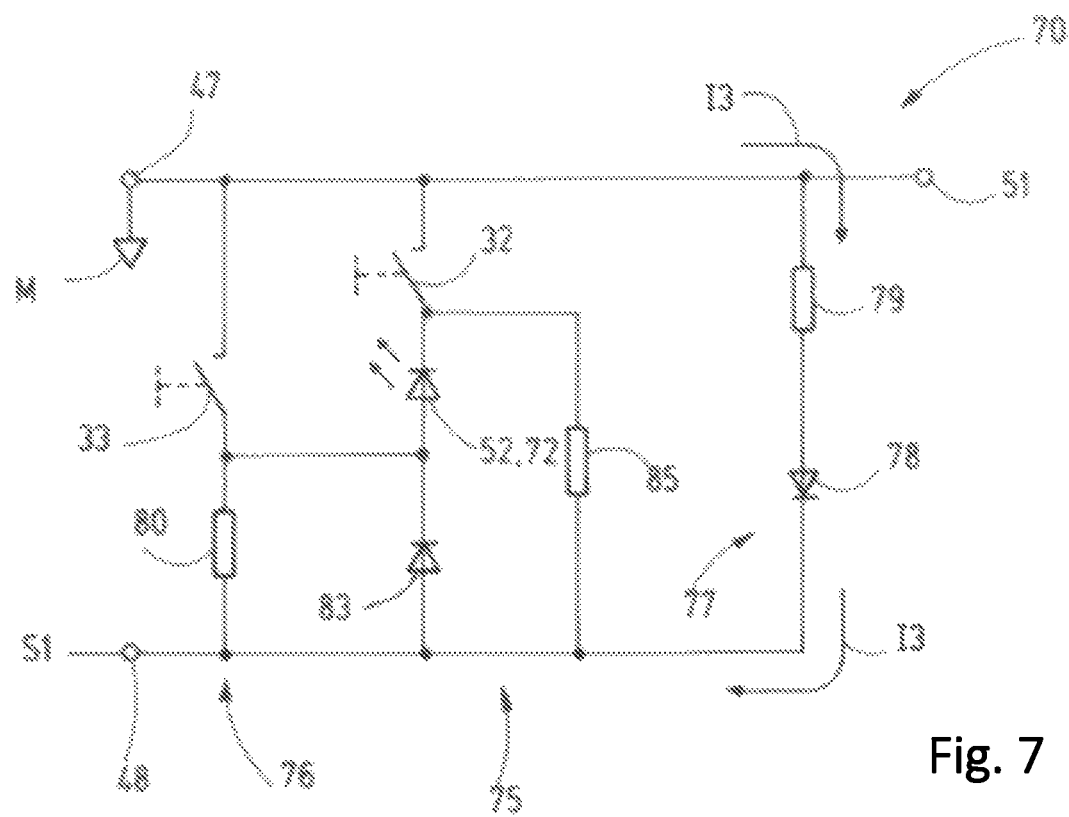

In the initial condition of the evaluation signal S it is assumed that both switches 32, 33 are non-operated and thus non-conductive (FIG. 7). Due to the negative potential at the signal connector 48, only a current flow from the ground connector 47 toward the signal connector 48 can occur. The first circuit branch 75 and the second circuit branch 76 are interrupted due to the non-conductive switches 32 and 33. Thus, only a third current I3 can flow through the third circuit branch 77. The amount of the third current I3 is evaluated in the evaluation circuit 40 and thereby it is recognized that the two switches 32, 33 are non-operated and thus non-conductive.

Figure 8:
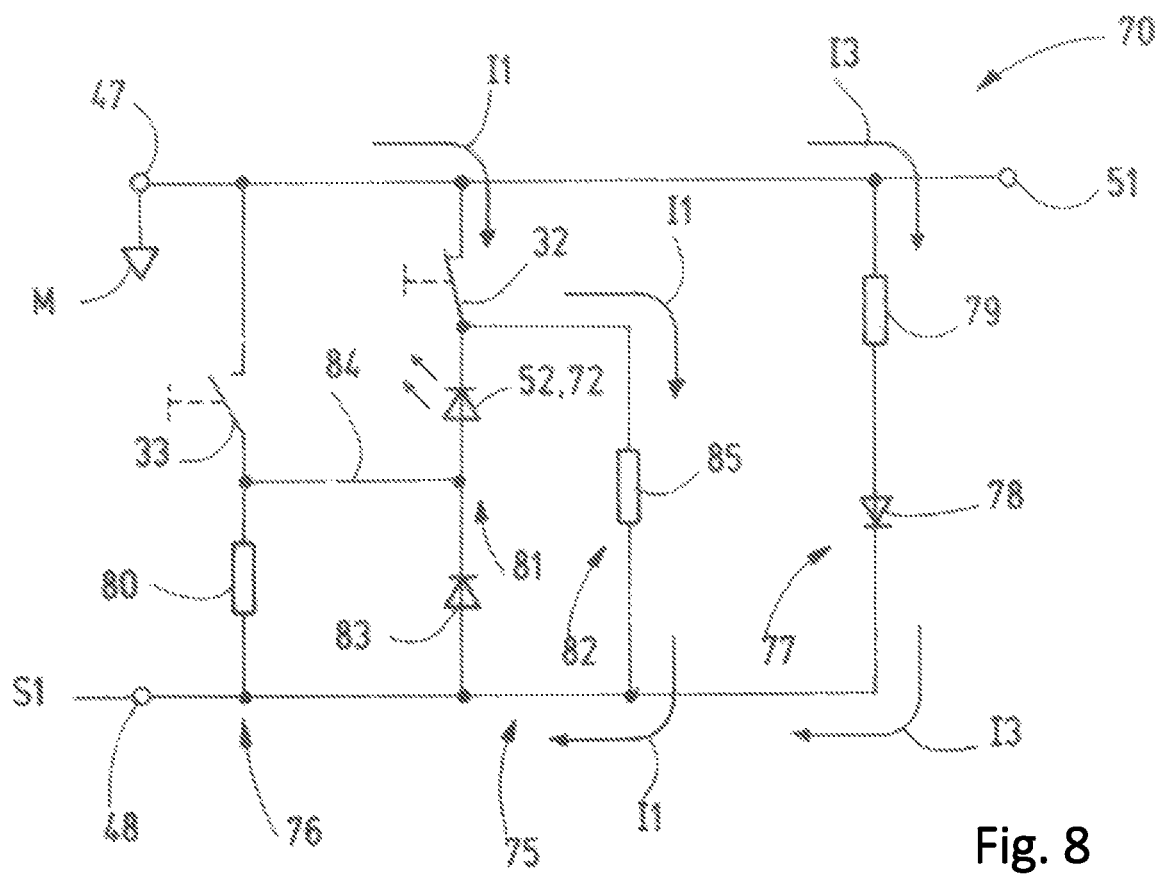

It is assumed that the operating person actuates the first switch 32 for requesting the cutting mode at a first time t1, such that it is switched in its conductive condition (FIG. 8). In addition to the third current I3 flowing through the third circuit branch 77, a first current I1 can now flow via the first switch 32 and through the fourth resistor 85 in the parallel current path 82. The total resistance of the control circuit 70 is obtained, therefore, substantially from the parallel connection of the second resistor 79 and the fourth resistor 85. The amount of the evaluation current corresponds to the sum of the amounts of the first current I1 and the second current I3 that changes compared with the non-actuated condition (FIG. 7). This change can be detected in the evaluation circuit 40.

Figure 5:
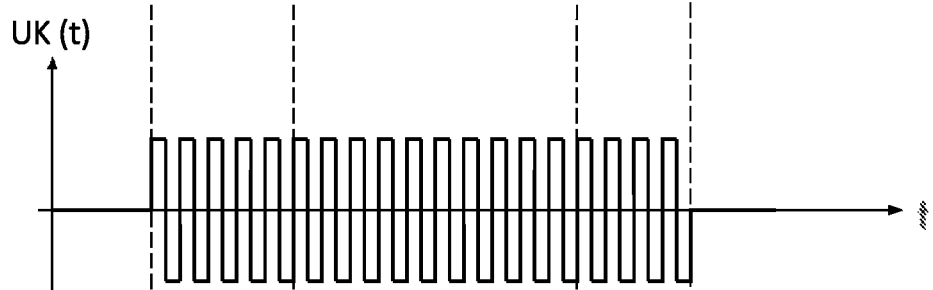

Thus, it is recognized in the apparatus 21 that an operating person has actuated the first switch 32. The evaluation circuit 40 is configured to start the cutting mode in this case and to control the instrument 26 accordingly. First, at the first time t1 the supply voltage UV is provided at the first apparatus output 22 via the activation signal W, such that a coagulation voltage UK is applied between the first coagulation output 50 and the second coagulation output 51 provided by the RF voltage source 42 (FIG. 5).

Beginning with the first time t1 at which the first switch 32 has been actuated, a first phase P1 starts in the cutting mode. During this first phase P1 the evaluation signal S maintains the first polarity S1, whereby the switch unit 53 takes its second switch condition. Then no cutting voltage US or no cutting current is provided at the cutting output 52. According to the example, the voltage and the current are substantially equal to zero at the cutting output 54 in the second switch condition of the switch unit 53. In a modified embodiment the switch unit 53 could establish a connection between the supply connector 46 and the cutting output 54 in the second switch condition in which the transformer 60 is bypassed such that the coagulation voltage UK is also applied to the cutting output 54.

The first phase P1 terminates, if a condition for termination of the first phase P1 is fulfilled, e.g. the termination of a predetermined time duration. In addition or as an alternative, a coagulation current through the apparatus 21 effectuated by the coagulation voltage UK can be evaluated and the first phase P1 can be terminated, if the coagulation current falls below a threshold.

After termination of the first Phase P1 (second time t2) a second phase P2 starts directly. In this second phase P2 a cutting voltage US is applied to the cutting output 54. For this the switch unit 53 must be switched from the second switch condition into the first switch condition. According to the example, this is achieved in that the evaluation circuit 40 changes the evaluation signal S during the second phase P2 such that it comprises alternating polarities S1, S2. The evaluation signal S can be an alternating voltage with positive and negative half-waves during this second phase P2. The amplitude of the positive and negative half-waves can have equal or different amounts. The duration of the positive half-waves and the negative half-waves can have equal or different lengths.

Figure 9:
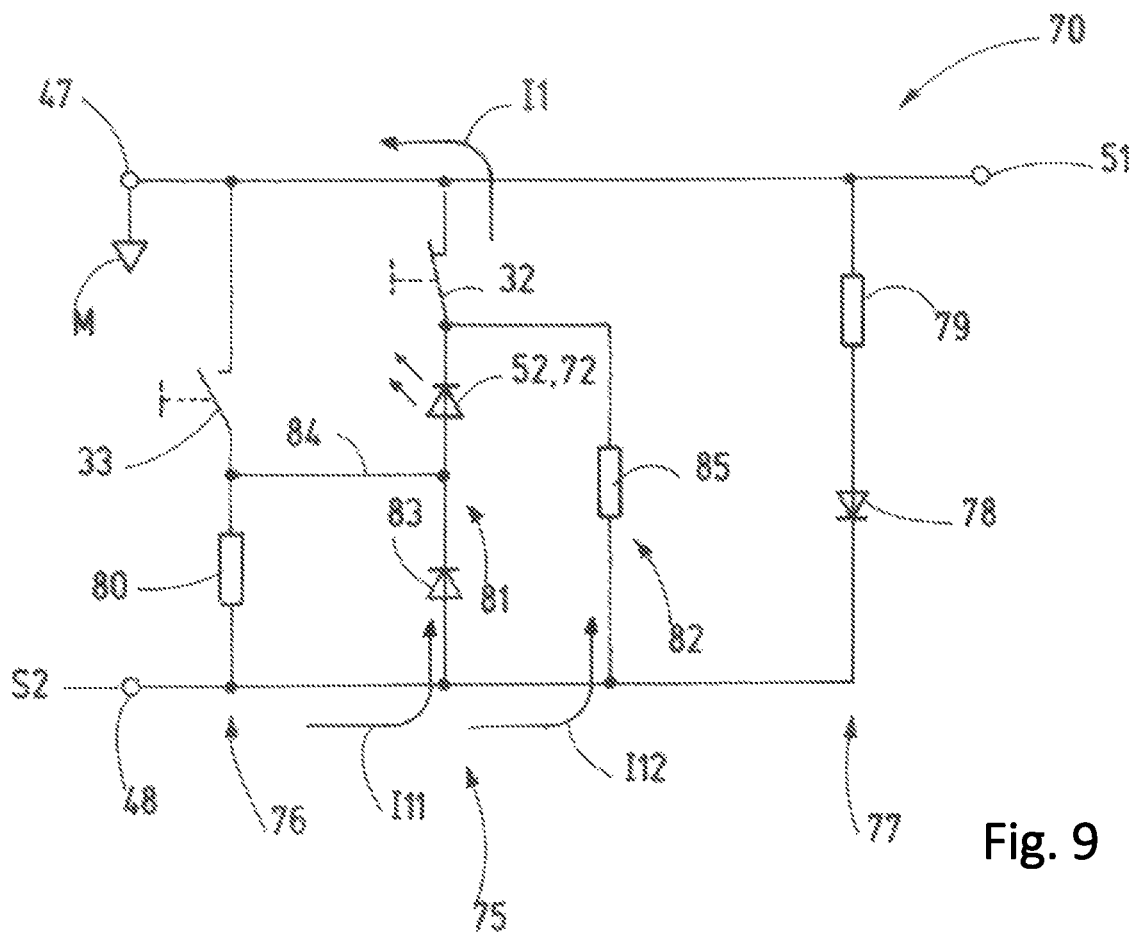

During the positive half-waves, if the evaluation signal S has the second polarity S2, the current flow direction is turned around in the control circuit 70 and the evaluation current flows from the signal connector 48 to the ground connector 47 (FIG. 9). The second circuit branch 76 is interrupted, due to the non-operated second switch 33 and a current flow through the third circuit branch 77 in the direction toward the ground connector 47 is impossible, due to the first diode 78. Only a first current I1 flows through the first circuit branch 75.

Thereby the first current I1 comprises a partial current I11 through the one-way current path 81 and a second partial current I12 through the parallel current path 82. The partial current I11 through the one-way current path 81 is remarkably higher than the second partial current I12 through the parallel current path 82, due to the less resistance value compared with the resistance value of the fourth resistor 85. The partial current I11 flows through the control element 52 that is concurrently the transmitter component 72 in the embodiment. In doing so, the control signal A is created and is transmitted to the receiver component 73. Thereupon the receiver component 73 initiates the switching of the switch unit 53 from the second switch condition to the first switch condition. In this first switch condition the at least one semiconductor switch 55 is conductive, such that an electrical connection between the switch ports 57 of the switch unit 53 is established. An electrical connection between the supply connector 46 and the tap 63 of the transformer 60 is established. This electrical connection provides for transformation of the supply voltage UV applied at the supply connector 46 into cutting voltage US by the transformer 60 provided at the cutting output 54 (FIG. 6).

The control signal A is formed by the light transmitted from the light emitting diode (transmitter component 72) of the optocoupler according to the example. The light emitting diode of the optocoupler 74 emits light only, if a current flows through the light emitting diode. The emitted light (control signal A) provides in turn for the creation of a voltage by the at least one photodiode of the optocoupler 74 that serves as source for creation of a drain source voltage or base-emitter voltage by the load and unload circuit 58, such that the at least one semiconductor switch 55 can be switched in the conductive condition or can be maintained in the conductive condition.

The second phase P2 terminates, if a condition for termination of the second phase P2 is fulfilled. This can be, for example, the termination of a predetermined duration for the second phase P2. The condition for termination of the second phase P2 can also be fulfilled, if a cutting current that flows from the cutting output 54 through the tissue drops below a threshold, which can be evaluated by the apparatus 21.

Figure 6:
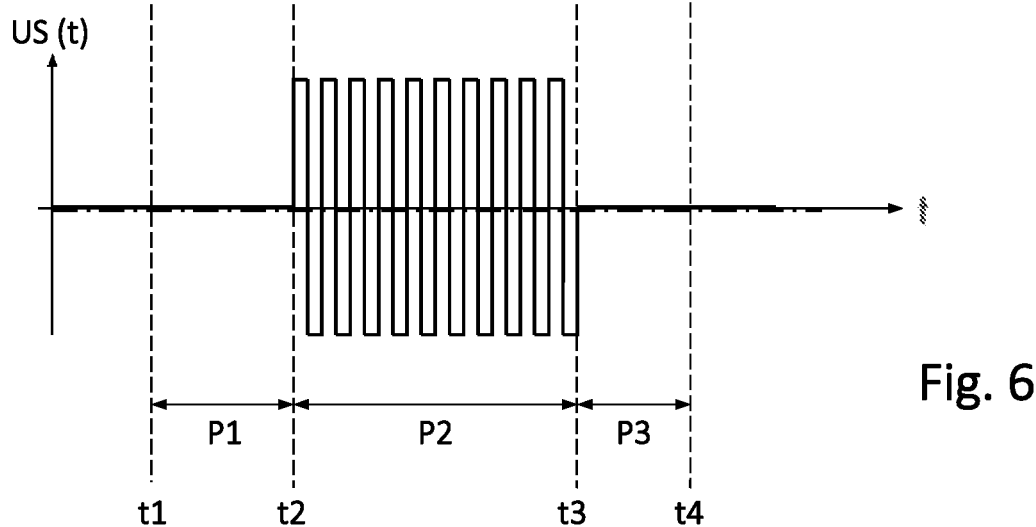

As illustrated in FIG. 6, the second phase P2 ends at a third time t3. At this time t3 a third phase P3 starts. During the third phase P3 the evaluation circuit 40 creates an evaluation signal S that corresponds to the initial condition and thus comprises only a first polarity S1, having a constant amount according to the example. The third phase P3 terminates, if a condition for termination of the third phase P3 is fulfilled, e.g. if a predetermined duration is terminated.

During the third phase P3 the coagulation voltage UK is maintained between the two coagulation outputs 50, 51. After termination of the third phase P3 (fourth time t4) the evaluation circuit 40 switches off the supply voltage UV by means of the activation signal W. The cutting is completed.

The third phase P3 is optional and can also be omitted.

Because the evaluation signal S comprises the first polarity S1 also at least during a time period during each of the phases P1, P2, P3, this at least one time period can be used to determine whether the first switch 32 is still operated. If the operating person releases the first switch 32 prior to termination of the cutting, this is determined and the supply voltage UV for the instrument 26 is switched off by means of the activation signal W. The cutting process can thus be interrupted in each phase P1, P2, P3 of the dissection.

Figure 10:
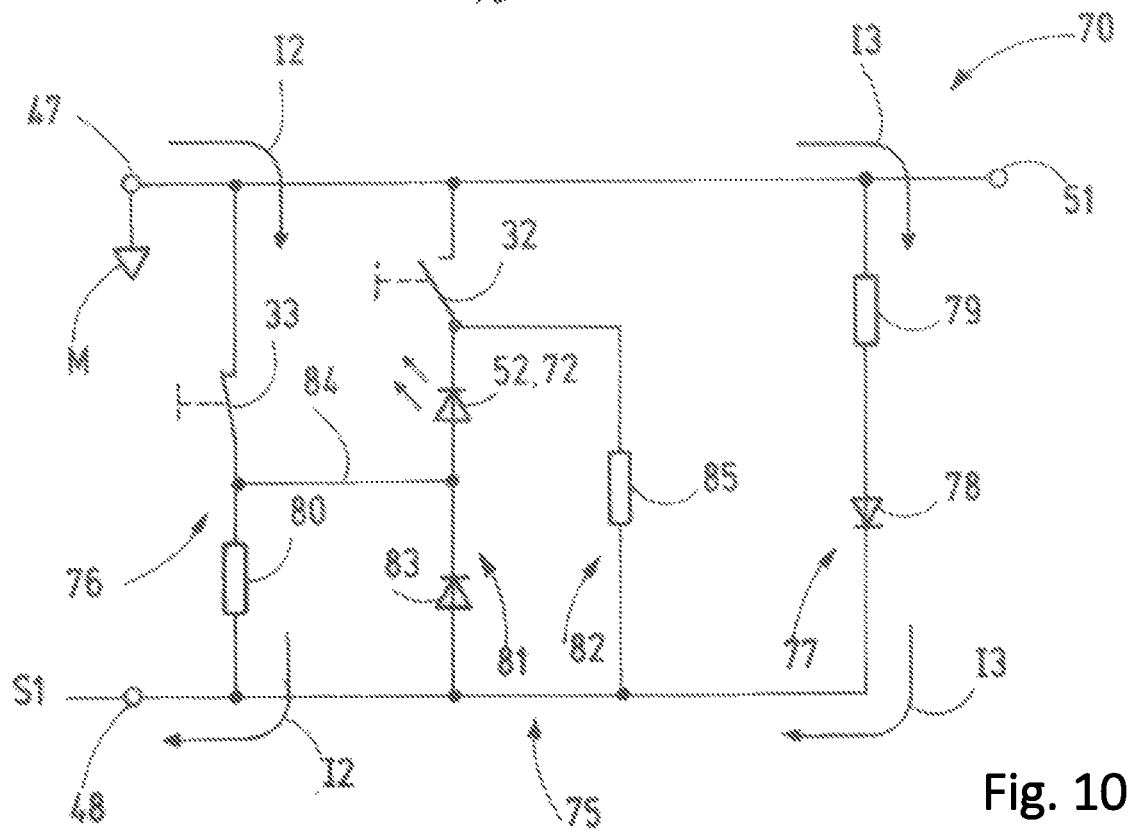

By way of example the situation is illustrated in FIG. 10 that the operating person operates the second switch 33 as long as an evaluation signal S is applied in its initial condition (first polarity S1 exclusively). In doing so, an evaluation current comprising a second current I2 through the second circuit branch 76, as well as a third current I3 through the third circuit branch 77 is created (FIG. 10). As already explained, the evaluation circuit 40 can detect the amount of the evaluation current formed by the sum of the second current I2 and the third current I3 and can detect that the second switch 33 has been operated. The total resistance of the control circuit 70 is obtained in this situation substantially by the parallel connection of the second resistor 79 and the third resistor 80.

Closing of the second switch 33 signalizes that the operating person requests the coagulation mode. By referring to FIGS. 4-6 it is assumed as an example that the second switch 33 has been operated at the first time t1. Analog to the cutting mode the application of the supply voltage UV at the first apparatus output 22 is initiated by the activation signal W by means of the evaluation circuit 40, such that the coagulation voltage UK is applied to the first coagulation output 50 (FIG. 5). The evaluation signal S is not modified in case of the request of the coagulation mode and maintains its initial condition. Thus, the switch unit 53 remains in its second switch condition and no cutting voltage US is applied to the cutting output 54 (dot-dashed line in FIG. 6).

Analog to the cutting mode, also in the coagulation mode the creation of a coagulation voltage UK can be linked to a termination condition and can be terminated by evaluation of the coagulation current or after termination of a duration according to the example, as already explained in connection with the cutting mode.

Figure 11:
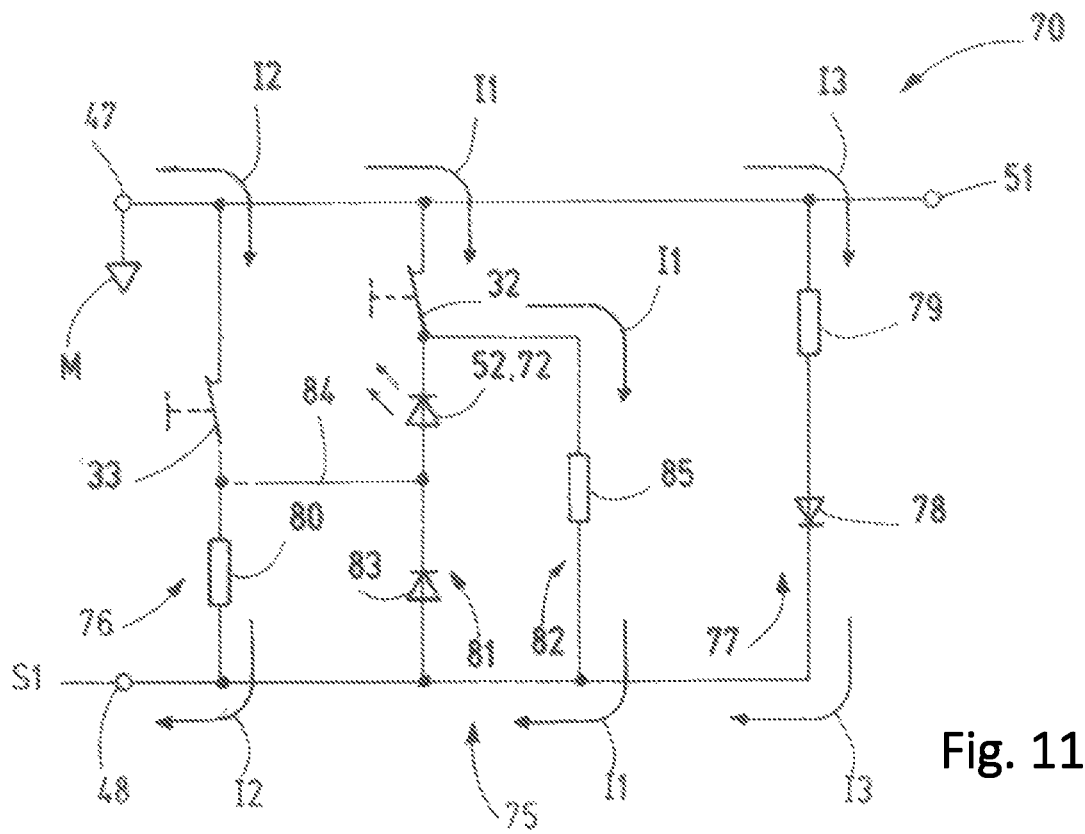

A situation is illustrated in FIG. 11 in that the operating person operates the first switch 32 as well as the second switch 33, if an evaluation signal S comprises its initial condition having exclusively the first polarity S1. In this case the amount of the evaluation current consists of the sum of the amounts of the first current I1 through the first circuit branch 75, the second current I2 through the second circuit branch 76, as well as the third current I3 through the third circuit branch 77. The total resistance of the control circuit 70 is obtained substantially by the parallel connection of the second resistor 79, the third resistor 80 and the fourth resistor 85. The evaluation circuit 40 of the apparatus 21 can thus determine that both switches 32, 33 have been actuated in that the amount of the evaluation current is evaluated.

One possibility in such a case is that the evaluation signal S maintains a condition having exclusively the first polarity S1 and only the coagulation mode is activated as described above. If the evaluation signal S does not comprise parts having the second polarity S2, no control signal A is generated that could switch the switch unit 53 in the first switch condition. The creation of a cutting voltage US for cutting is omitted.

Figure 12:
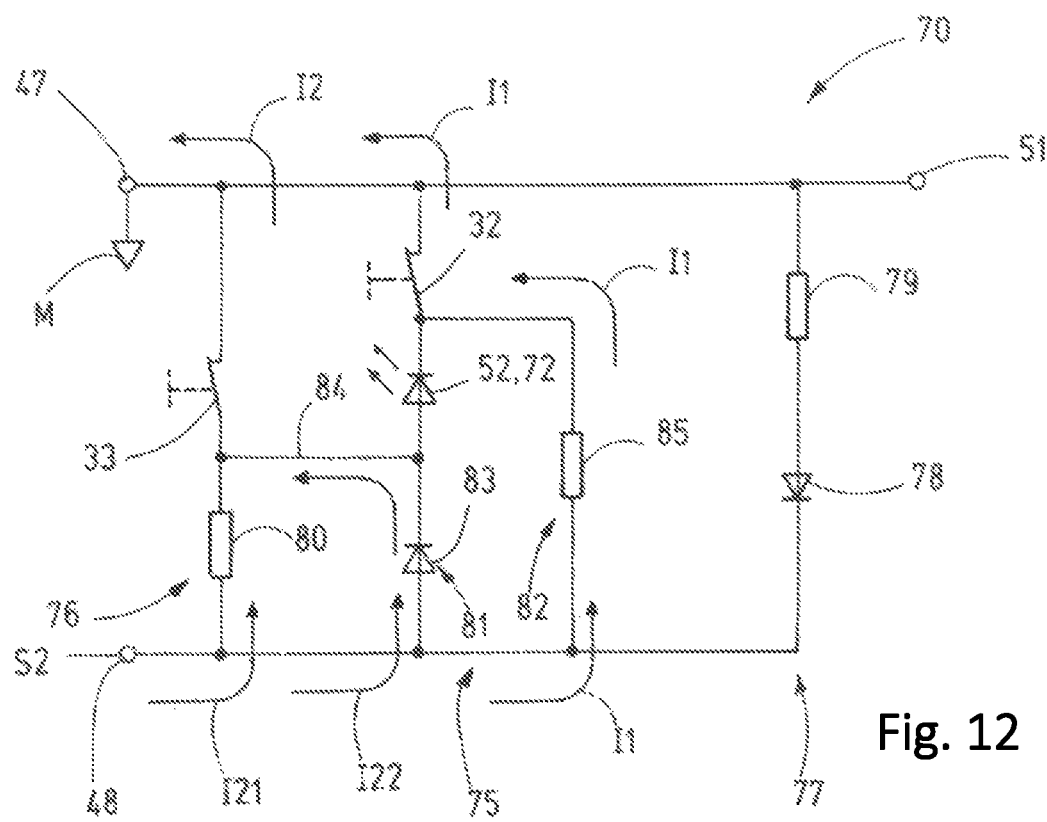

Even if analog to the cutting mode the evaluation signal S comprises a period with alternating polarity S1, S2, the switching of the switch unit 53 in the first switch condition is impeded (compare FIG. 12). In that the second switch 33 bypasses the control element 52 a current flow through the control element 52 is avoided and in so doing, no control signal A is generated that could initiate the switching of the switch unit 53 in the first switch condition. Also in this case the creation of a cutting voltage US is avoided.

The at least one receiver component 73 is connected with the control port 56 of each semiconductor switch 55 via the load and unload circuit 58 in order to be able to maintain charges in the control ports 56 sufficiently long on one hand (at least during the duration of a first half-wave having the first polarity S1) and to dissipate the charges again that are present there on the other hand, if the switch unit 53 shall be switched in the second switch condition.

In the embodiment the charge in the gate connections of the MOSFETs is maintained via the load and unload circuit 58, such that the switch unit 53 remains in its second switch condition (conducting condition) also if a half-wave having the first polarity S1 is present during the second phase P2. At least for the duration of a half-wave having the first polarity S1, the charge in the gates of the MOSFETs is maintained by the load and unload circuit 58, if the photodiodes of the optocoupler 74 are again controlled by the light emitting diode of the optocoupler 74, if the first switch 32 is conductive during a second half-wave S2.

An embodiment of a load and unload circuit 58 is illustrated in FIG. 13. It is clear that also other load and unload circuits could be used.

The at least one receiver component 73 has a first port 73a of higher electrical potential (here: anode side of the at least one photodiode) and a second port 73b of lower electrical potential (here: cathode side of the at least one photodiode). At the first port 73a a higher potential is applied than at the second port 73b during an activation by the transmitter component 72.

A fifth resistor 90 is connected parallel to the at least one receiver component 73. An anode of a third diode 91 is connected with the first port 73a, the cathode of which is connected with a fourth capacitor 92. The other side of the fourth capacitor 92 is connected with the second port 73b. The fifth resistor 90 is connected parallel to the series connection of the third diode 91 and the fourth capacitor 92.

A series connection of a fourth diode 93 and a fifth capacitor 94 is connected parallel to the third diode 91, wherein the anode of the fourth diode 93 is connected with a cathode of the third diode 91. The cathode of the fourth diode 93 is connected with the anode of a fifth diode 95. The cathode of the fifth diode 95 is connected with a sixth capacitor 96. The other connection of the sixth capacitor 96 is connected with the second port 73b. In addition, the sixth capacitor 96 is connected between the control ports 56 (drain connections) and the connection point between the two semiconductor switches 55 (source connections) connected in series. A sixth resistor 97 is connected parallel to the sixth capacitor 96.

Multiple cascades of one diode 91, 93, 95 and a capacitor 92, 94, 96 connected in series respectively serve to voltage multiplication of the voltage applied to the at least one receiver component 73 during activation by the transmitter component 72. Due to the provided capacitors, the activation of the semiconductor switches 55 and according to the example, the charge in the gates of the field effect transistors can be maintained also if during a short period no voltage is applied to the at least one receiver component 73 during a half-wave having the first polarity S1. The capacitors thus serve as buffer capacitors. In order to allow unloading, the resistors 90, 97 of the load and unload circuit 58 are provided. If the first switch 32 is non-activated, the charges in the control ports 56 can level via the resistors 90, 97 and the semiconductor switches 55 can return to their blocking conditions. The duration beginning with switching of the first switch 32 in the non-conductive condition until the blocking of the semiconductor switches 55 depends on the dimensioning of the components that are present in the load and unload circuit 58.

In modification to the above-described load and unload circuit 58, also more or less cascades of diodes and capacitors can be used. This depends on which voltage is required for activation of the semiconductor switches 55.

Figure 14:
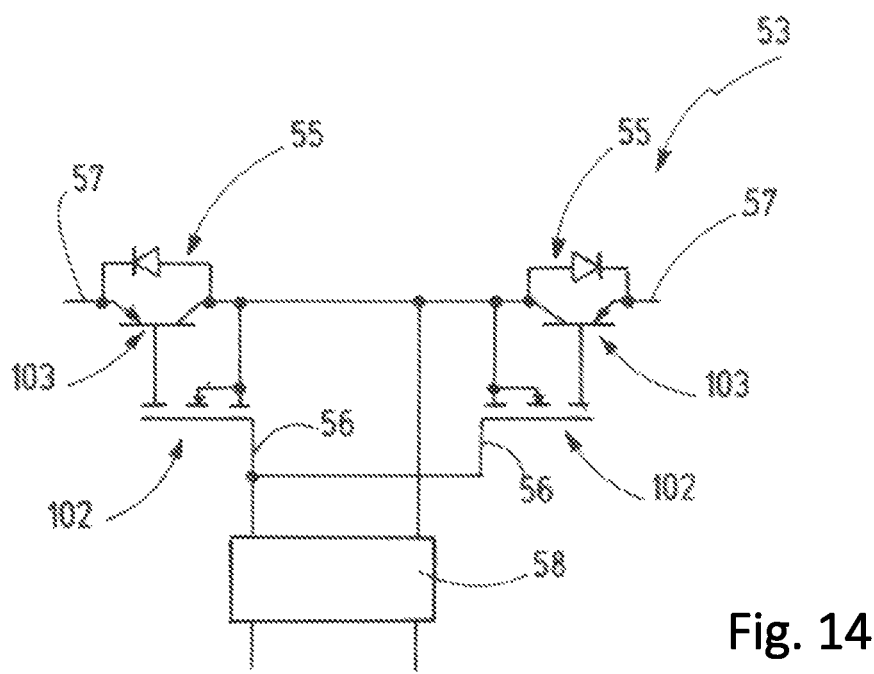

FIG. 14 illustrates a modified embodiment of the switch unit 53. The semiconductor switches 55 comprise bipolar transistors 103 and are respectively controlled by a semiconductor control switch 102. The semiconductor control switches 102 are field effect transistors, normally non-conductive n-channel MOSFETs according to the example. The control ports 56 of the semiconductor control switches 102 are connected with the load and unload circuit 58. In addition, the two collectors of the bipolar transistors 103 are connected with the load and unload circuit 58. Each emitter of one bipolar transistor 103 forms a switch port 57. The collectors of the bipolar transistors 103 are in addition connected with the source connections of the field effect transistors that form the semiconductor control switches 102. The basis of each bipolar transistor 103 is connected with a drain connection of a respective assigned field effect transistor. As soon as the gate source voltage is sufficiently high, the semiconductor control switches 102 become conductive such that a base current flows from the PNP-bipolar transistors 103 and they transition to their conductive condition.

Figure 15:
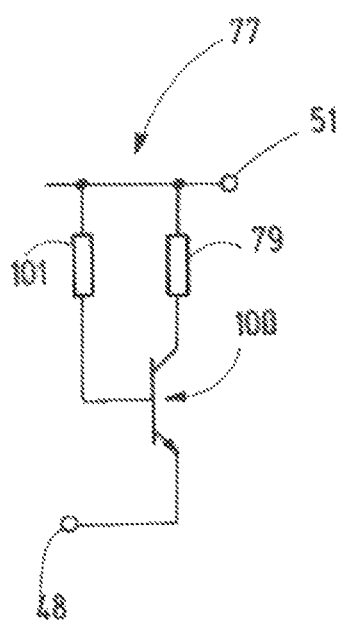

A modified embodiment of the third circuit branch 77 is shown in FIG. 15. Instead of the first diode 78, a transistor, particularly a bipolar transistor, can be used, the collector connection of which is connected with the second resistor 79 and the emitter connection of which is connected with the signal connector 48. The base connection of the transistor is connected with ground via a seventh resistor 101.

The invention refers to a device 20 as well as a method for coagulation and/or dissection of biological tissue. The device 20 comprises an apparatus 21 and an instrument 26 electrically connected with the apparatus 21. On the instrument 26 at least a first switch 32 is provided for manual operation that is part of an operation circuit 45. An evaluation circuit 40 of the apparatus 21 provides an evaluation signal S for the instrument 26. In addition, the apparatus 21 can create a supply voltage UV or alternatively a supply current IV and provide it for the instrument 26. In the initial condition the evaluation signal S comprises only one polarity and is in the initial condition either always higher or equal to zero or else always less or equal to zero, however not continuously, but at most temporarily equal to zero. The evaluation signal S is provided to a control circuit 70 of the instrument 26 in which a characteristic of the evaluation signal S is adjusted depending on the operating condition of the first switch 32. The evaluation circuit 40 of the apparatus 21 detects this characteristic and can determine thereupon whether an operating person activates a cutting mode via the first switch 32. Thereupon the evaluation circuit 40 can cause the apparatus 21 to provide a supply voltage UV or a supply current IV for the instrument 26 and the evaluation signal S is changed according to the requested cutting mode, particularly with regard to its polarity S1, S2. In the cutting mode the evaluation signal S comprises at least temporarily also the second polarity S2.

LIST OF REFERENCE SIGNS 20 device for coagulation and cutting
21 apparatus 22 first apparatus output
23 third apparatus output
24 second apparatus output
25 cable
26 instrument
27 housing
28 handle
29 tool
30 connection part
31 operating element
32 first switch
33 second switch
34 jaw
35 jaw
36 first coagulation electrode
37 second coagulation electrode
38 cutting electrode
39 counter support
40 evaluation circuit
41 hinge
42 voltage source
45 operation circuit
46 supply connector
47 ground connector
48 signal connector
49 first capacitor
50 first coagulation output
51 second coagulation output
52 control element
53 switch unit
54 cutting output
55 semiconductor switch
56 control port
57 switch port
58 load and unload circuit
60 transformer
61 primary winding
62 secondary winding
63 tap
64 second capacitor
65 third capacitor
66 first resistor
70 control circuit
71 coupling device
72 transmitter component
73 receiver component
73a first port
73b second port
74 optocoupler
75 first circuit branch
76 second circuit branch
77 third circuit branch
78 first diode
79 second resistor
80 third resistor
81 one-way current path
82 parallel current path
83 second diode
84 connection current path
85 fourth resistor
90 fifth resistor
91 third diode
92 fourth capacitor
93 fourth diode
94 fifth capacitor
95 fifth diode
96 sixth capacitor
97 sixth resistor
100 transistor
101 seventh resistor
102 semiconductor control switch
103 bipolar transistor
A control signal
I current
I1 first current
I11 partial current
I12 partial current
I2 second current
I21 partial current
I22 partial current
I3 third current
IV supply current
M ground
P1 first phase
P2 second phase
P3 third phase
S evaluation signal
S1 first polarity
S2 second polarity
t1 first time
t2 second time
t3 third time
t4 fourth time
UK coagulation voltage
US cutting voltage
UV supply voltage

The invention claimed is:

1. A device (20) for coagulation and/or cutting of biological tissue comprising:
an apparatus (21) and an instrument (26) electrically connected with the apparatus (21) wherein the apparatus (21) is configured to provide a supply voltage (UV) or a supply current (IV) at a first apparatus output (22) and wherein the apparatus (21) comprises an evaluation circuit (40) that is configured to provide an evaluation signal (S) at a second apparatus output (24);
wherein an operation circuit (45) of the instrument (26) comprises:
a supply connector (46) configured to be connected with the first apparatus output (22), a signal connector (48) configured to be connected with the second apparatus output (24);
a control circuit (70) connected with the signal connector (48), the control circuit configured to create a control signal (A) that depends on a polarity (S1, S2) of the evaluation signal (S), wherein the control circuit comprises a manually operable first switch (32);
a switch unit (53) configured to be controlled by the control signal (A) and configured to be switched between a first switch condition and a second switch condition and that is connected with the supply connector (46) and a cutting output (54);
wherein the control circuit (70) is configured to adjust a characteristic of the evaluation signal (S) depending on an operating condition of the first switch (32) and wherein the evaluation circuit (40) is configured to detect the characteristic of the evaluation signal (S) and to adjust the polarity (S1, S2) of the evaluation signal (S) depending on the characteristic.

2. The device according to claim 1, wherein the evaluation circuit is configured such that if the characteristic of the evaluation signal (S) indicates that the first switch (32) has been operated, the evaluation signal (S) comprises only a first polarity (S1) during a first phase (P1, P3) beginning with the operation of the first switch (32) and comprises the first polarity (S1) and a second polarity (S2) opposed to the first polarity (S1) in an alternating manner during a second phase (P2).

3. The device according to claim 2, wherein the control circuit (70) is configured to cause the switch unit (53) to take the first switch condition via the control signal (A), if during the second phase (P2) the evaluation signal (S) comprises at least temporarily the second polarity (S2), wherein an electrical cutting voltage (US) or an electrical cutting current is provided at the cutting output (54) in the first switch condition that is suitable for cutting of biological tissue.

4. The device according to claim 2, wherein the control circuit (70) is configured to cause the switch unit (53) to take the second switch condition via the control signal (A), if during the first phase (P1) the evaluation signal (S) comprises only the first polarity (S1), wherein no electrical cutting voltage (US) and no electrical cutting current is provided at the cutting output (54) in the second switch condition.

5. The device according to claim 1, wherein the apparatus (21) comprises a controllable voltage source (42) or current source and wherein the evaluation circuit (40) is configured to control the voltage source (42) or current source via an activation signal (W).

6. The device according to claim 1, wherein the control circuit (70) comprises a manually operable second switch (33).

7. The device according to claim 6, wherein the control circuit (70) is configured to adjust the characteristic of the evaluation signal (S) depending on the operation condition of the second switch (33) and wherein the evaluation circuit (40) is configured to detect the characteristic of the evaluation signal (S) and to adjust the polarity (S1, S2) of the evaluation signal (S) depending on the characteristic.

8. The device according to claim 7, wherein the evaluation circuit (40) is configured to create an activation signal (W) such that a controllable voltage source (42) or current source provides the supply voltage (UV) or the supply current (IV) at the first apparatus output (22), if the characteristic of the evaluation signal (S) indicates that the first switch (32) and/or the second switch (33) have been actuated.

9. The device according to claim 7, wherein the evaluation circuit (40) is configured to create the evaluation signal (S) comprising only the first polarity (S1), if the characteristic of the evaluation signal (S) indicates that the second switch (33) has been actuated.

10. The device according to claim 1, wherein the control circuit (70) is configured to adjust an amount of the evaluation signal (S) as the characteristic of the evaluation signal (S) depending on the operating condition of the first switch (32).

11. The device according to claim 1, wherein the instrument (26) comprises a tool (29) having at least one cutting electrode (38), at least one first coagulation electrode (36) and at least one second coagulation electrode (37).

12. The device according to claim 11, wherein the cutting output (54) is connected with the at least one cutting electrode (38) and wherein a first coagulation output (50) of the operation circuit (45) is connected with the at least one first coagulation electrode (36) and a second coagulation output (S1) of the operation circuit (45) is connected with the at least one second coagulation electrode (37).

13. The device according to claim 1, wherein the first switch (32) and a control element (52) configured for creation of the control signal (A) are connected in series in a first circuit branch (75), wherein the first circuit branch (75) is connected with the signal connector (48).

14. A instrument according to claim 13, wherein the control circuit (70) comprises a manually operable second switch (33) that is arranged in a second circuit branch (76), wherein the second circuit branch (76) is connected with the signal connector (24).

15. The instrument according to claim 1, wherein the operation circuit (45) comprises a transformer circuit (60) that is connected with the supply connector (46) on a primary side of the transformer circuit and with the cutting output (54) on a secondary side of the transformer circuit.

16. A method for coagulation and/or cutting of biological tissue implementing an apparatus (21) and an instrument (26) that is electrically connected with the apparatus (21), wherein the apparatus (21) comprises a first apparatus output (22) for a supply voltage (UV) or a supply current (IV) and an evaluation circuit (40) connected with a second apparatus output (24), wherein the instrument (26) comprises an operation circuit (45), wherein the operation circuit (45) comprises a supply connector (46) configured to be connected with the first apparatus output (22), a signal connector (48) configured to be connected with the second apparatus output (24), a control circuit (70) connected with the signal connector (48), a manually operable first switch (32) and a switch unit (53) that is connected with the supply connector (46) and a cutting output (54), wherein the method comprises the following steps:

creating an evaluation signal (S) by the evaluation circuit (40) and providing the evaluation signal (S) at the second apparatus output (24), receiving the evaluation signal (S) and adjusting a characteristic of the evaluation signal (S) depending on an operating condition of the first switch (32) by the control circuit (70), detecting the characteristic of the evaluation signal (S) and adjusting a polarity (S1, S2) of the evaluation signal (S) depending on the detected characteristic of the evaluation signal (S) by the evaluation circuit (40), creating a control signal (A) depending on the polarity (S1, S2) of the evaluation signal (S) by the control circuit (70), controlling the switch unit (53) to take a first switch condition or a second switch condition via the control signal (A).

* * * * *